United States Patent
Akashi et al.

(10) Patent No.: US 8,222,349 B2
(45) Date of Patent: Jul. 17, 2012

(54) BIOABSORBABLE MATERIAL AND IN-VIVO INDWELLING DEVICE MADE THEREOF

(75) Inventors: Mitsuru Akashi, Osaka (JP); Michiya Matsusaki, Osaka (JP); Yotaro Fujita, Shizuoka (JP); Makoto Onishi, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 116 days.

(21) Appl. No.: 12/886,913

(22) Filed: Sep. 21, 2010

(65) Prior Publication Data

US 2011/0046309 A1 Feb. 24, 2011

Related U.S. Application Data

(63) Continuation of application No. PCT/JP2009/053929, filed on Mar. 3, 2009.

(30) Foreign Application Priority Data

Mar. 27, 2008 (JP) .................................. 2008-084376

(51) Int. Cl.
*C08G 63/64* (2006.01)
*A61F 2/02* (2006.01)
*C08G 63/06* (2006.01)

(52) U.S. Cl. ........ 525/450; 525/462; 525/469; 528/206; 528/392; 623/23.75

(58) Field of Classification Search .................. 525/450, 525/462, 469; 526/269; 528/206, 392; 623/23.75
See application file for complete search history.

(56) References Cited

U.S. PATENT DOCUMENTS

| 5,614,599 A * | 3/1997 | Bales et al. .................... 525/461 |
| 6,716,957 B2 * | 4/2004 | Tunc ............................. 528/354 |
| 2005/0018123 A1 | 1/2005 | Kaneko et al. |
| 2006/0018870 A1 | 1/2006 | Kuriyama et al. |

FOREIGN PATENT DOCUMENTS

| JP | 2004-250700 A | 9/2004 |
| JP | 2006-63316 A | 3/2006 |

OTHER PUBLICATIONS

International Search Report (PCT/ISA/210) issued on Jun. 9, 2009, by Japanese Patent Office as the International Searching Authority for International Application No. PCT/JP2009/053929.
Mitsuri Akashi et al., Engineering Plastics of Environmental Recycling Type, Journal of the Institute of Polymer Science, pp. 870-873, Nov. 2006, Japan.

* cited by examiner

*Primary Examiner* — Fred M Teskin
(74) *Attorney, Agent, or Firm* — Buchanan Ingersoll & Rooney PC

(57) ABSTRACT

A bioabsorbable material which is flexible and degradable at a controlled rate, and an in-vivo indwelling device made thereof. The bioabsorbable material is a copolymer composed of an aromatic compound having an $\alpha,\beta$-unsaturated carboxylic group and at least one hydroxyl group as substituents on the aromatic ring, and a polycarbonate or a monomer constituting polycarbonate. Alternatively, it is a copolymer composed of, as the first component, an aromatic compound having an $\alpha,\beta$-unsaturated carboxylic group and at least one hydroxyl group as substituents on the aromatic ring, as the second component, an aromatic compound having an $\alpha,\beta$-unsaturated carboxylic group and at least two hydroxyl groups as substituents on the aromatic ring, and, as the third component, a polycarbonate or a monomer constituting polycarbonate.

20 Claims, No Drawings

BIOABSORBABLE MATERIAL AND IN-VIVO INDWELLING DEVICE MADE THEREOF

CROSS-REFERENCE TO RELATED APPLICATION

This application is a continuation of International Application No. PCT/JP2009/053929 filed on Mar. 3, 2009, and claims priority to Japanese Application No. 2008-84376 filed on Mar. 27, 2008, the entire contents of both of which are incorporated by reference herein.

TECHNICAL FIELD

Exemplary aspects of the present invention relate to a bioabsorbable material and an in-vivo indwelling device made thereof.

BACKGROUND

Plastics have developed along with the advance of chemistry. Nowadays, plastics find use in various fields as a highly functional material substituting metal, and have become established as an indispensable material in the industry. The use of plastics is expanding from daily necessities to industries and atomic, space, and ocean technologies. Plastics are incomparable with other materials because of their characteristic properties and potential, such as light weight, good moldability for complicatedly shaped products, good corrosion resistance, and good chemical resistance. On the other hand, they are inferior in heat resistance to metal. In order to overcome such shortcomings, new polymers having good heat resistance and high strength and elastic modulus have been developed in the 1960s based on the past research concerning polymer science. The thus developed polymers are called engineering plastics, which are characterized by a heat distortion temperature higher than 100° C., a tensile strength higher than 60 MPa, and an elastic modulus higher than 2 GPa.

There has recently arisen a necessity for development of new plastics compatible with environment (i.e., degradable and non-toxic) to cope with the issues of environmental destruction and resource depletion. Plant-derived polymers (called green polymer or green-based polymer) are attracting attention. One of their typical examples is polylactic acid. However, it is not satisfactory in strength and heat resistance.

A liquid-crystalline polyester was developed in 1976. It is the first liquid-crystalline engineering plastics ever produced by modifying polyethylene terephthalate (PET) with p-hydroxybenzoic acid (PHB) for improvement in heat resistance. This development led to exploitation of new products such as liquid-crystalline polyarylate (types I and II). Nevertheless, nothing has been reported so far about engineering plastics that solve the foregoing problems.

With the foregoing in mind, M. Akashi et al. attempted to develop new liquid-crystalline engineering plastics by paying attention to 4-hydroxycinnamic acid (4HCA) as the plant-derived reactive rigid substance. Up to that time, there had been no report about 4HCA homopolymer (or poly-4HCA), except for those about synthesis and granulation. Akashi et al. found for the first time that poly-4HCA (belonging to polyesters derived from nature) exhibits nematic liquid-crystal. This polymer is reactive with light and compatible with living bodies, and it also has good heat resistance required of engineering plastics. However, it has a disadvantage of being brittle and poor in solubility and processability, presumably due to low molecular weight and rigid skeleton.

In order to address this problem, they adopted an idea of copolymerizing with a natural material that imparts flexibility to the skeleton of poly-4HCA and turned their attention to 3,4-dihydroxycinnamic acid (caffeic acid) (DHCA) which is a 4HCA derivative. This copolymer is obtained by polycondensation with heating at 200° C. for 6 hours in the presence of acetic anhydride (as an ester exchange agent) and sodium acetate (as a catalyst). Despite introduction of DHCA, the copolymer remains solid up to 25° C. and becomes fluid upon heating, with an apparent band pattern showing. This phenomenon proves the copolymer to be a liquid crystal. The liquid-crystallizing temperature falls to 150° C. and the weight-decreasing temperature exceeds 300° C. with the increasing amount of DHCA. The resulting copolymer has a broad liquid-crystalline temperature range and is easy to handle. Moreover, it has a high molecular weight essential for strength and elastic modulus. A compression test show that, in regard to strength and elastic modulus, it exhibits a high Young's modulus and breaking strength comparable to polycarbonate (which is a typical engineering plastics) when the content of DHCA is 50 to 100 mol %, although it depends on the composition ratio of copolymer. See Non-Patent Document 1. Unfortunately, this copolymer is rigid but hard and brittle (lacking flexibility) and slow in degradation.

Non-Patent Document 1: Engineering Plastics of Environmental Recycling Type, by M. Akashi, Journal of the Institute of Polymer Science "Kobunshi," November.

SUMMARY

According to an exemplary aspect, a bioabsorbable material is provided which is flexible and degradable at a controlled rate. According to another exemplary aspect, an in-vivo indwelling device is provided made of said bioabsorbable material.

The foregoing exemplary aspects can be achieved through the following exemplary aspects (1) to (15).

(1) A bioabsorbable material which comprises a copolymer composed of an aromatic compound having an α,β-unsaturated carboxylic group and at least one hydroxyl group as substituents on the aromatic ring, and a polycarbonate or a monomer constituting polycarbonate.

(2) The bioabsorbable material as defined in the aspect (1), in which the aromatic compound is any of 2-hydroxycinnamic acid, 3-hydroxycinnamic acid, 4-hydroxycinnamic acid, 4-hydroxy-2-methoxycinnamic acid, 4-hydroxy-3-methoxycinnamic acid, and 3,4-dihydroxycinnamic acid.

(3) The bioabsorbable material as defined in the aspects (1) or (2), in which the polycarbonate or the monomer constituting polycarbonate is composed of trimethylene carbonate or ethylene carbonate.

(4) The bioabsorbable material as defined in any of the aspects (1) to (3), in which the copolymer is at least one species or more than one species in combination selected from the group consisting of block copolymers, random copolymers, and graft copolymers.

(5) The bioabsorbable material as defined in the aspect (1), in which the aromatic compound is one which has at least one iodine group as a substituent on the aromatic ring.

(6) The bioabsorbable material as defined in the aspect (1), which is represented by the general formula 1 below.

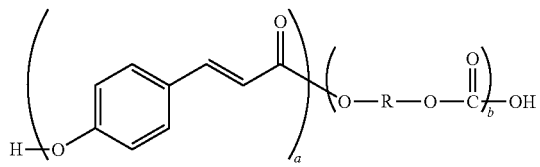

Formula 1 where R denotes $(CH_2)_n$, with n being 1 to 5, a denotes 10 to 10,000, and b denotes 10 to 10,000.

(7) An in-vivo indwelling device made of the bioabsorbable material as defined in any of the aspects (1) to (6).

(8) A bioabsorbable material which comprises a copolymer composed of, as the first component, an aromatic compound having an α,β-unsaturated carboxylic group and at least one hydroxyl group as substituents on the aromatic ring, as the second component, an aromatic compound having an α,β-unsaturated carboxylic group and at least two hydroxyl groups as substituents on the aromatic ring, and, as the third component, a polycarbonate or a monomer constituting polycarbonate.

(9) The bioabsorbable material as defined in the aspect (8), in which the aromatic compound as the first component is any of 2-hydroxycinnamic acid, 3-hydroxycinnamic acid, 4-hydroxycinnamic acid, 4-hydroxy-2-methoxycinnamic acid, and 4-hydroxy-3-methoxycinnamic acid.

(10) The bioabsorbable material as defined in the aspects (8) or (9), in which the aromatic compound as the second component is 3,4-dihydroxycinnamic acid.

(11) The bioabsorbable material as defined in any of the aspects (8) to (10), in which the polycarbonate or the monomer constituting polycarbonate is composed of trimethylene carbonate or ethylene carbonate.

(12) The bioabsorbable material as defined in any of the aspects (8) to (11), in which the copolymer is at least one species or more than one species in combination selected from the group consisting of block copolymers, random copolymers, and graft copolymers.

(13) The bioabsorbable material as defined in the aspect (8), in which the aromatic compound as the first component is one which has at least one iodine group as a substituent on the aromatic ring.

(14) The bioabsorbable material as defined in the aspect (8), which is represented by the general formula 2 below.

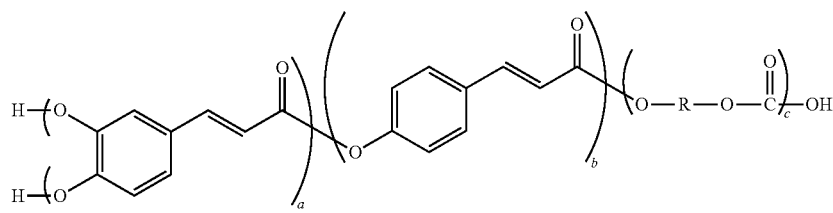

Formula 2 where R denotes $(CH_2)_n$, with n being 1 to 5, a denotes 10 to 10,000, b denotes 10 to 10,000, and c denotes 10 to 10,000.

(15) An in-vivo indwelling device made of the bioabsorbable material as defined in any of the aspects (8) to (14).

An exemplary bioabsorbable material according to one aspect is a copolymer composed of an aromatic compound having an α,β-unsaturated carboxylic group and at least one hydroxyl group as substituents on the aromatic ring, and a polycarbonate or a monomer constituting polycarbonate, or a copolymer composed of, as the first component, an aromatic compound having an α,β-unsaturated carboxylic group and at least one hydroxyl group as substituents on the aromatic ring, as the second component, an aromatic compound having an α,β-unsaturated carboxylic group and at least two hydroxyl groups as substituents on the aromatic ring, and, as the third component, a polycarbonate or a monomer constituting polycarbonate. Therefore, it can be flexible and degradable at a controlled rate, and it can also be suitable for molding into an in-vivo indwelling device such as a stent.

DETAILED DESCRIPTION

The following is a detailed description of an exemplary bioabsorbable material and an exemplary in-vivo indwelling device made thereof.

The First Embodiment

The bioabsorbable material according to a first exemplary embodiment is a copolymer formed from an aromatic compound having an α,β-unsaturated carboxylic group and at least one hydroxyl group as substituents on the aromatic ring, and a polycarbonate or a monomer constituting polycarbonate. Therefore, it can be flexible and degradable at a controlled rate.

The aromatic compound can be exemplified by 2-hydroxycinnamic acid, 3-hydroxycinnamic acid, 4-hydroxycinnamic acid, 4-hydroxy-2-methoxycinnamic acid, 4-hydroxy-3-methoxycinnamic acid, and 3,4-dihydroxycinnamic acid. 4-hydroxycinnamic acid can be exemplary, because it can give a bioabsorbable material which exhibits high safety in the living body and high mechanical strength as desired.

The polycarbonate or the monomer constituting polycarbonate can include, for example, trimethylene carbonate or ethylene carbonate, with trimethylene carbonate being exemplary, because it can give a bioabsorbable material which exhibits high safety in the living body and desirable tensile strain (at break).

The copolymer can include, for example, at least one species or more than one species in combination selected from block copolymers, random copolymers, and graft copolymers. Block copolymers can be exemplary because they can give a bioabsorbable material which exhibits high mechanical strength as desired on account of their high stereoregularity.

The aromatic compound mentioned above can have at least one iodine group as a substituent on the aromatic ring. The iodine group can make the bioabsorbable material visible through X-rays.

The iodine-substituted aromatic compound can include, for example, 4-hydroxy-3,5-diiodocinnamic acid. It can give a bioabsorbable material which exhibits high safety in the living body and high mechanical strength as desired.

The bioabsorbable material according to the first embodiment in an exemplary form can be one which is represented by the general formula 1 below.

Formula 1

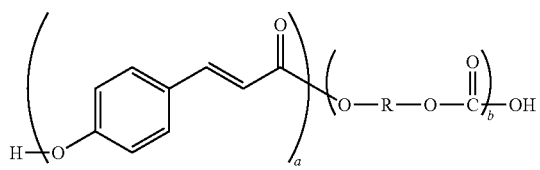

where R denotes $(CH_2)_n$, with n being 1 to 5, a denotes 10 to 10,000, and b denotes 10 to 10,000.

Such exemplary bioabsorbable material can be formed from 4-hydroxycinnamic acid which is an aromatic compound having an α,β-unsaturated carboxylic group and at least one hydroxyl group as substituents on the aromatic ring. It can give a bioabsorbable material which exhibits high safety in the living body and high mechanical strength as desired.

The bioabsorbable material according to the first embodiment in an exemplary form is one which is represented by the general formula 3 below.

Formula 3

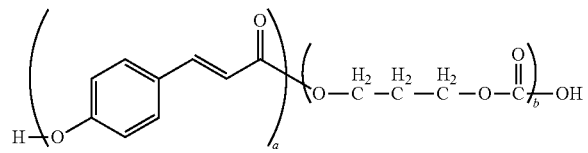

where a denotes 10 to 10,000 and b denotes 10 to 10,000.

Such exemplary bioabsorbable material can be formed from 4-hydroxycinnamic acid which is an aromatic compound having an α,β-unsaturated carboxylic group and at least one hydroxyl group as substituents on the aromatic ring, and trimethylene carbonate which is a monomer constituting polycarbonate. It can give a bioabsorbable material which exhibits high safety in the living body and desirable tensile strain (at break).

The bioabsorbable material according to the first embodiment can have a number-average molecular weight (Mn) of 8,000 to 1,000,000 and a molecular weight distribution (Mw/Mn) of 1.01 to 5.00 (which is defined as the ratio of weight-average molecular weight to number-average molecular weight). These values can vary depending on use.

The bioabsorbable material according to the first embodiment can have a tensile strength of 10 to 800 MPa, a Young's modulus of 500 to 30,000 MPa, and a tensile stain (at break) of 10 to 600%, in tests measured in conformity with JIS K7113.

The bioabsorbable material according to the first embodiment can be degradable such that it decreases in the number-average molecular weight by 1 to 30% and 1 to 50% after immersion for 2 weeks and 4 weeks, respectively, in a phosphoric acid buffer solution of pH 7.2 (at 37° C.).

The bioabsorbable material according to the first embodiment can be produced in any way without specific restrictions. An exemplary method is by polycondensation of the first component (which is an aromatic compound having an α,β-unsaturated carboxylic group and at least one hydroxyl group as substituents on the aromatic ring) and the second component (which is a polycarbonate or a monomer constituting polycarbonate) in the presence of a catalyst (which is sodium acetate) and an ester exchange agent (which is acetic anhydride).

As mentioned above, the bioabsorbable material according to the first embodiment can be flexible and degradable at a controlled rate. Therefore, it can be suitable for molding into an in-vivo indwelling device such as a stent.

The Second Embodiment

The bioabsorbable material according to a second exemplary embodiment is a copolymer formed from, as the first component, an aromatic compound having an α,β-unsaturated carboxylic group and at least one hydroxyl group as substituents on the aromatic ring, as the second component, an aromatic compound having an α,β-unsaturated carboxylic group and at least two hydroxyl groups as substituents on the aromatic ring, and, as the third component, a polycarbonate or a monomer constituting polycarbonate. It can be flexible and degradable at a controlled rate.

The aromatic compound as the first component can include, for example, 2-hydroxycinnamic acid, 3-hydroxycinnamic acid, 4-hydroxycinnamic acid, 4-hydroxy-2-methoxycinnamic acid, and 4-hydroxy-3-methoxycinnamic acid. 4-hydroxycinnamic acid can be exemplary, because it can give a bioabsorbable material which exhibits high safety in the living body and mechanical strength as desired.

The aromatic compound as the second component can be 3,4-dihydroxycinnamic acid. The use of 3,4-dihydroxycinnamic acid can give a bioabsorbable material which exhibits high safety in the living body and better mechanical strength.

The polycarbonate or the monomer constituting polycarbonate can include, for example, trimethylene carbonate or ethylene carbonate, with trimethylene carbonate being exemplary, because it can give a bioabsorbable material which exhibits high safety in the living body and a desirable tensile strain (at break).

The copolymer can include, for example, at least one species or more than one species in combination selected from block copolymers, random copolymers, and graft copolymers. Block copolymers can be exemplary because they can give a bioabsorbable material which exhibits high mechanical strength as desired on account of their high stereoregularity.

The aromatic compound as the first component mentioned above can have at least one iodine group as a substituent on the aromatic ring. The iodine group can make the bioabsorbable material visible through X-rays.

The iodine-substituted aromatic compound as the first component can include, for example, 4-hydroxy-3,5-diiodocinnamic acid. It can give a bioabsorbable material which exhibits high safety in the living body and high mechanical strength as desired.

The bioabsorbable material according to the second embodiment in an exemplary form can be one which is represented by the general formula 2 below.

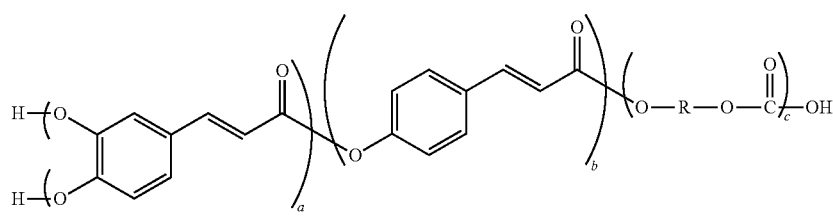

Formula 2 where R denotes $(CH_2)_n$, with n being 1 to 5, a denotes 10 to 10,000, b denotes 10 to 10,000, and c denotes 10 to 10,000.

Such exemplary bioabsorbable material can be formed from, as the first component, 4-hydroxycinnamic acid which is an aromatic compound having an α,β-unsaturated carboxylic group and at least one hydroxyl group as substituents on the aromatic ring, and it also be formed from, as the second component, 3,4-dihydroxycinnamic acid (caffeic acid) which is an aromatic compound having an α,β-unsaturated carboxylic group and at least two hydroxyl group as substituents on the aromatic ring. It can give a bioabsorbable material which exhibits high safety in the living body and better tensile strength.

The bioabsorbable material according to the second embodiment in an exemplary form is one which is represented by the general formula 4 below.

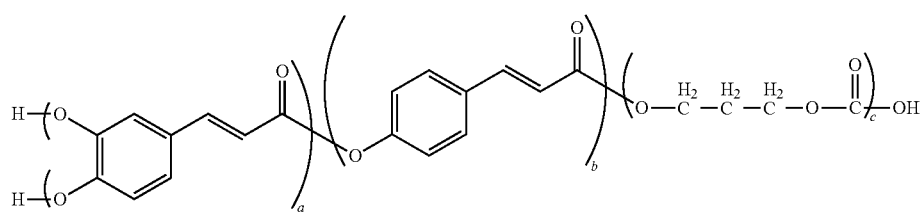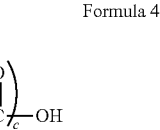

Formula 4 where a denotes 10 to 10,000, b denotes 10 to 10,000, and c denotes 10 to 10,000.

Such exemplary bioabsorbable material can be formed from, as the first component, 4-hydroxycinnamic acid which is an aromatic compound having an α,β-unsaturated carboxylic group and at least one hydroxyl group as substituents on the aromatic ring, as the second component, 3,4-dihydroxycinnamic acid (caffeic acid) which is an aromatic compound having an α,β-unsaturated carboxylic group and at least two hydroxyl group as substituents on the aromatic ring, and as the third component, trimethylene carbonate which is a monomer constituting polycarbonate. It can give a bioabsorbable material which exhibits high safety in the living body and desirable tensile strain (at break).

The bioabsorbable material according to the second embodiment can have a number-average molecular weight (Mn) of 8,000 to 1,000,000 and a molecular weight distribution (Mw/Mn) of 1.01 to 5.00 (which is defined as the ratio of weight-average molecular weight to number-average molecular weight). These values can vary depending on use.

The bioabsorbable material according to the second embodiment can have a tensile strength of 10 to 800 MPa, a Young's modulus of 500 to 30,000 MPa, and a tensile stain (at break) of 10 to 600%, in tests measured in conformity with JIS K7113.

The bioabsorbable material according to the second embodiment can be degradable such that it decreases in the number-average molecular weight by 1 to 30% and 1 to 50% after immersion for 2 weeks and 4 weeks, respectively, in a phosphoric acid buffer solution of pH 7.2 (at 37° C.).

The bioabsorbable material according to the second embodiment can be produced in any way without specific restrictions. An exemplary method is by polycondensation of the first component (which is an aromatic compound having an α,β-unsaturated carboxylic group and at least one hydroxyl group as substituents on the aromatic ring), the second component (which is an aromatic compound having an α,β-unsaturated carboxylic group and at least two hydroxyl group as substituents on the aromatic ring), and the third component (which is a polycarbonate or a monomer constituting polycarbonate) in the presence of a catalyst (which is sodium acetate) and an ester exchange agent (which is acetic anhydride).

As mentioned above, the bioabsorbable material according to the second embodiment can be flexible and degradable at a controlled rate. Therefore, it can be suitable for molding into an in-vivo indwelling device such as a stent.

EXAMPLES

Exemplary aspects will be described in more detail with reference to the examples.

Example 1

An oligomer was prepared from 0.066 g of 4-hydroxycinnamic acid (4HCA) and 8.16 g of trimethylene carbonate monomer (TMC), mixed with 20 μL of tin octoate (in an atmosphere replaced with nitrogen three times), by stirring at 150° C. for 6 hours on an oil bath under a nitrogen stream. The resulting solids were dissolved in chloroform and reprecipitated from methanol. The precipitate was filtered with suction and then vacuum-dried for 48 hours at room temperature. Thus there was obtained the desired product (Oligo-TMC) which has a number-average molecular weight (Mn) of 21,800.

Then, a copolymer was prepared from 2.05 g of 4-hydroxycinnamic acid (4HCA) and 5.45 g of Oligo-TMC by polycondensation in a three-neck flask containing 0.05 g of sodium acetate (as a catalyst) and 50 mL of acetic anhydride (as an ester exchange agent). The reaction, which was preceded by nitrogen bubbling for 10 minutes, was carried out by stirring at 180° C. for 6 hours on an oil bath under a nitrogen stream. The resulting solids were dissolved in dimethylformamide and reprecipitated from methanol. The precipitate was filtered with suction and then vacuum-dried for 48 hours at room temperature. Thus there was obtained the desired product (4HCA-TMC copolymer).

The 4HCA-TMC copolymer was found to have a tensile strength of 56.2 MPa, a Young's modulus of 8,700 MPa, and a tensile strain of 83% (at break) by tensile test conforming to JIS K7113.

The 4HCA-TMC copolymer was dissolved in chloroform to give a 1 wt % solution. The solution was cast into film (about 200 µm thick), which was subsequently vacuum-dried for 24 hours at room temperature. A circular specimen (10 mm in diameter) was punched out from the cast film. The specimen was immersed in 20 mL of phosphoric acid buffer solution (pH 7.2) contained in a 30 mL sample bottle for hydrolysis at 37° C. for 2 weeks and 4 weeks. It was found that the specimen decreased in number-average molecular weight by 2% and 16%, respectively, after immersion for 2 weeks and 4 weeks.

Example 2

An oligomer was prepared from 0.066 g of 4-hydroxycinnamic acid (4HCA) and 8.16 g of trimethylene carbonate monomer (TMC), mixed with 20 µL of tin octoate (in an atmosphere replaced with nitrogen three times), by stirring at 150° C. for 6 hours on an oil bath under a nitrogen stream. The resulting solids were dissolved in chloroform and reprecipitated from methanol. The precipitate was filtered with suction and then vacuum-dried for 48 hours at room temperature. Thus there was obtained the desired product (Oligo-TMC) which has a number-average molecular weight (Mn) of 21,800.

Then, a copolymer was prepared from 2.52 g of 3,4-dihydroxycinnamic acid (caffeic acid), 5.45 g of the Oligo-TMC, and 2.05 g of 4-hydroxycinnamic acid (4HCA) by polycondensation in a three-neck flask containing 0.05 g of sodium acetate (as a catalyst) and 50 mL of acetic anhydride (as an ester exchange agent). The reaction, which was preceded by nitrogen bubbling for 10 minutes, was carried out by stirring at 180° C. for 6 hours on an oil bath under a nitrogen stream. The resulting solids were dissolved in dimethylformamide and reprecipitated from methanol. The precipitate was filtered with suction and then vacuum-dried for 48 hours at room temperature. Thus there was obtained the desired product (DHCA-4HCA-TMC copolymer).

The DHCA-4HCA-TMC copolymer was found to have a tensile strength of 72.5 MPa, a Young's modulus of 10,500 MPa, and a tensile strain of 97% (at break) by tensile test conforming to JIS K7113.

The DHCA-4HCA-TMC copolymer was dissolved in chloroform to give a 1 wt % solution. The solution was cast into film (about 200 µm thick), which was subsequently vacuum-dried for 24 hours at room temperature. A circular specimen (10 mm in diameter) was punched out from the cast film. The specimen was immersed in 20 mL of phosphoric acid buffer solution (pH 7.2) contained in a 30 mL sample bottle for hydrolysis at 37° C. for 2 weeks and 4 weeks. It was found that the specimen decreased in number-average molecular weight by 3% and 11%, respectively, after immersion for 2 weeks and 4 weeks.

Comparative Example 1

A homopolymer was prepared from 9.00 g of 4-hydroxycinnamic acid (4HCA), mixed with 0.05 g of sodium acetate (as a catalyst) and 50 mL of acetic anhydride (as an ester exchange agent) in a three-neck flask (which underwent nitrogen bubbling for 10 minutes), by stirring at 200° C. for 6 hours on an oil bath under a nitrogen stream. The resulting solids were dissolved in dimethylformamide and reprecipitated from methanol. The precipitate was filtered with suction and then vacuum-dried for 48 hours at room temperature. Thus there was obtained the desired product (poly-4HCA).

The poly-4HCA was too hard and brittle to be made into a specimen for tensile test.

1 g of the poly-4HCA (in powder form) was immersed in 20 mL of phosphoric acid buffer solution (pH 7.2) contained in a 30 mL sample bottle for hydrolysis at 37° C. for 2 weeks and 4 weeks. The sample became insoluble in any solvent, which made it impossible to measure the decrease in number-average molecular weight by GPC.

Comparative Example 2

A copolymer was prepared from 5.4 g of 3,4-dihydroxycinnamic acid (caffeic acid) (DHCA) and 4.9 g of 4-hydroxycinnamic acid (4HCA) by polycondensation in a three-neck flask containing 0.05 g of sodium acetate (as a catalyst) and 50 mL of acetic anhydride (as an ester exchange agent). The reaction, which was preceded by nitrogen bubbling for 10 minutes, was carried out by stirring at 200° C. for 6 hours on an oil bath under a nitrogen stream. The resulting solids were dissolved in dimethylformamide and reprecipitated from methanol. The precipitate was filtered with suction and then vacuum-dried for 48 hours at room temperature. Thus there was obtained the desired product (DHCA-4HCA copolymer).

The DHCA-4HCA copolymer was too hard and brittle to be made into a specimen for tensile test.

1 g of the DHCA-4HCA copolymer (in powder form) was immersed in 20 mL of phosphoric acid buffer solution (pH 7.2) contained in a 30 mL sample bottle for hydrolysis at 37° C. for 2 weeks and 4 weeks. The sample did not decrease in number-average molecular weight at all after immersion for 2 weeks and 4 weeks. The detailed description above describes embodiments of the bioabsorbable material and in-vivo indwelling device. However it is to be understood that the invention is not limited to those precise embodiments and variations described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A bioabsorbable material comprising a copolymer formed from an aromatic compound including an α,β-unsaturated carboxylic group and at least one hydroxyl group as substituents on the aromatic ring, and a polycarbonate or a monomer constituting polycarbonate.

2. The bioabsorbable material as defined in claim 1, wherein the aromatic compound is selected from the group consisting of 2-hydroxycinnamic acid, 3-hydroxycinnamic acid, 4-hydroxycinnamic acid, 4-hydroxy-2-methoxycinnamic acid, 4-hydroxy-3-methoxycinnamic acid, 3,4-dihydroxycinnamic acid, and a combination thereof.

3. The bioabsorbable material as defined in claim 1, wherein the polycarbonate or the monomer constituting polycarbonate comprises trimethylene carbonate or ethylene carbonate.

4. The bioabsorbable material as defined in claim 1, wherein the copolymer is at least one species or more than one species in combination selected from the group consisting of block copolymers, random copolymers, and graft copolymers.

5. The bioabsorbable material as defined in claim 1, wherein the aromatic compound includes at least one iodine group as a substituent on the aromatic ring.

6. The bioabsorbable material as defined in claim 1, which is represented by formula 1:

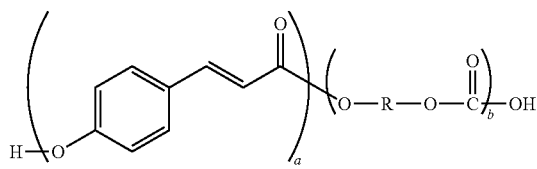

Formula 1 wherein R represents $(CH_2)_n$, with n being 1 to 5, a represents 10 to 10,000, and b represents 10 to 10,000.

7. An in-vivo indwelling device formed from the bioabsorbable material as defined in claim 1.

8. A bioabsorbable material comprising a copolymer formed from, as a first component, an aromatic compound including an α,β-unsaturated carboxylic group and at least one hydroxyl group as substituents on the aromatic ring; as a second component, an aromatic compound including an α,β-unsaturated carboxylic group and at least two hydroxyl groups as substituents on the aromatic ring; and, as a third component, a polycarbonate or a monomer constituting polycarbonate.

9. The bioabsorbable material as defined in claim 8, wherein the aromatic compound as the first component is selected from the group consisting of 2-hydroxycinnamic acid, 3-hydroxycinnamic acid, 4-hydroxycinnamic acid, 4-hydroxy-2-methoxycinnamic acid, 4-hydroxy-3-methoxycinnamic acid, and a combination thereof.

10. The bioabsorbable material as defined in claim 8, wherein the aromatic compound as the second component is 3,4-dihydroxycinnamic acid.

11. The bioabsorbable material as defined in claim 8, wherein the polycarbonate or the monomer constituting polycarbonate comprises trimethylene carbonate or ethylene carbonate.

12. The bioabsorbable material as defined in claim 8, wherein the copolymer is at least one species or more than one species in combination selected from the group consisting of block copolymers, random copolymers, and graft copolymers.

13. The bioabsorbable material as defined in claim 8, wherein the aromatic compound as the first component includes at least one iodine group as a substituent on the aromatic ring.

14. The bioabsorbable material as defined in claim 8, which is represented by the formula 2:

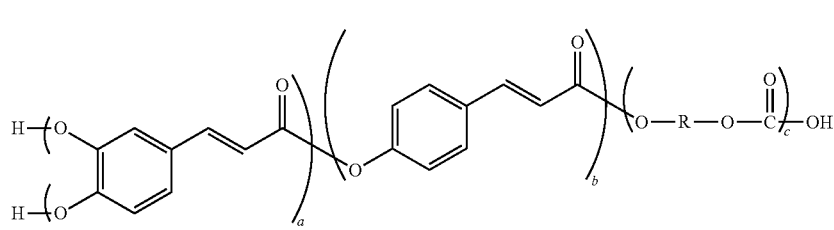

Formula 2 wherein R represents $(CH_2)_n$, with n being 1 to 5, a represents 10 to 10,000, b represents 10 to 10,000, and c represents 10 to 10,000.

15. An in-vivo indwelling device formed from the bioabsorbable material as defined in claim 8.

16. The bioabsorbable material as defined in claim 2, wherein the polycarbonate or the monomer constituting polycarbonate comprises trimethylene carbonate or ethylene carbonate.

17. The bioabsorbable material as defined in claim 2, wherein the copolymer is at least one species or more than one species in combination selected from the group consisting of block copolymers, random copolymers, and graft copolymers.

18. The bioabsorbable material as defined in claim 9, wherein the aromatic compound as the second component is 3,4-dihydroxycinnamic acid.

19. The bioabsorbable material as defined in claim 9, wherein the polycarbonate or the monomer constituting polycarbonate comprises trimethylene carbonate or ethylene carbonate.

20. The bioabsorbable material as defined in claim 9, wherein the copolymer is at least one species or more than one species in combination selected from the group consisting of block copolymers, random copolymers, and graft copolymers.

* * * * *